United States Patent [19]

Hellmuth et al.

[11] 3,966,622
[45] June 29, 1976

[54] LUBE OIL DISPERSANT OF IMPROVED ODOR AND ANTIOXIDANT PROPERTIES

[75] Inventors: Walter W. Hellmuth, Beacon; Harry Chafetz, Poughkeepsie; William P. Cullen, Fishkill, all of N.Y.

[73] Assignee: Texaco Inc., New York, N.Y.

[22] Filed: Sept. 9, 1974

[21] Appl. No.: 504,616

Related U.S. Application Data

[62] Division of Ser. No. 330,914, Feb. 9, 1973.

[52] U.S. Cl. ............................... 252/46.6; 260/125; 260/128
[51] Int. Cl.² .......................................... C10M 1/48
[58] Field of Search ............ 260/125, 128; 252/46.6

[56] References Cited
UNITED STATES PATENTS

| | | | |
|---|---|---|---|
| 2,773,861 | 12/1956 | Musselman | 252/46.6 X |
| 3,201,438 | 8/1965 | Reed | 252/46.6 X |
| 3,272,744 | 9/1966 | Schallenberg et al. | 252/46.6 X |
| 3,285,853 | 11/1966 | Lacoste | 252/46.6 |
| 3,389,086 | 6/1968 | Reed et al. | 252/46.7 |

*Primary Examiner*—Helen M. S. Sneed
*Attorney, Agent, or Firm*—T. H. Whaley; C. G. Ries; Robert A. Kulason

[57] ABSTRACT

In the method of preparing sulfurized, alkoxylated, inorganic phosphorus acid free, steam hydrolyzed polyalkene-$P_2S_5$ reaction product useful as a detergent-dispersant in lubricating oil compositions of improved antioxidant and odor properties comprising contacting polyalkene and $P_2S_5$ in the presence of a catalytic amount of sulfur to form the polyalkene-$P_2S_5$ reaction product, contacting the resultant polyalkene-$P_2S_5$ reaction product with steam to form an inorganic phosphorus acid containing hydrolyzed polyalkene-$P_2S_5$ reaction product, removing inorganic phosphorus acid from the hydrolyzed polyalkene-$P_2S_5$ reaction product, contacting the inorganic acid free, hydrolyzed polyalkene-$P_2S_5$ reaction product with alkylene oxide, the improvement which comprises the step selected from the group consisting of 1). contacting said inorganic acid free, steam hydrolyzed polyalkene-$P_2S_5$ intermediate product with added sulfur, and 2). contacting the alkoxylated, inorganic phosphorus acid free, steam hydrolyzed polyalkene-$P_2S_5$ reaction product with added sulfur. The invention is also directed to the resultant sulfurized alkoxylated product and lubricant compositions thereof.

8 Claims, No Drawings

LUBE OIL DISPERSANT OF IMPROVED ODOR AND ANTIOXIDANT PROPERTIES

This is a division, of application Ser. No. 330,914, filed Feb. 9, 1973.

BACKGROUND OF INVENTION

Alkoxylated, inorganic phosphorus acid free, steam hydrolyzed polyalkene-$P_2S_5$ reaction products hereinafter also referred to as the alkoxylated product have long been known as superior detergent-dispersants in lubricating oils. The standard method of preparation of these alkoxylated products is first reacting a polyalkene with $P_2S_5$ to form the polyalkene-$P_2S_5$ reaction product, this reaction preferably conducted in the presence of a catalytic amount of sulfur, e.g., between about 0.1 and 1 wt. % to facilitate the reaction. The resultant reaction product is then hydrolyzed with steam followed by the removal of formed inorganic phosphorus acid by-products therefrom. The steam hydrolyzed inorganic phosphorus acid free polyalkene-$P_2S_5$ reaction product is then alkoxylated to form the alkoxylated product. In the absence of inorganic acid the alkoxylation results in essentially a monoalkoxylated as opposed to a polyalkoxylated product. This resultant product has been characterized in the past by the formula:

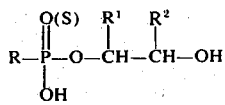

where R is hydrocarbyl and $R^1$ and $R^2$ are hydrogen or alkyl. Since the product in essence is a complex mixture of many compounds including ring compounds containing phosphorus and sulfur in the ring as well as phosphoric and thiophosphoric structures, definition of the product in terms of process appears suitable.

Although these prior alkoxylated products are excellent detergent-dispersants, they have been evidencing some undesirable properties when utilized in the recently developed high temperature automotive engines fitted with anti-pollution devices. Specifically, under the aforementioned conditions they appear to contribute to the sometimes substantial increase of lubricant compositions containing same. Investigation has determined that this undesired oil thickening is partially the result of the oxidative breakdown of the alkoxylated detergent-dispersant triggered by excessibly high engine temperature coupled with the funneling of ever increasing amounts of engine exhaust into the crankcase for anti-pollution treatment. One means of counteracting this oxidative tendency was to include antioxidants in the lube formulations such as the alkylated diphenylamines. Although the added antioxidants successfully retarded the oxidative decomposition of the alkoxylated product, they have the undesired feature of contributing to the excessive quantities of additives required in modern day engine oils as well as being another factor adding to the cost of said oils.

Another ever present problem with the alkoxylated products is the harsh sulfurous odor evolving in the initial use of lubricating compositions containing said alkoxylated products. This odor is believed caused by the evolution of volatile sulfurous materials loosely held in a chemical sense in the reaction product. In the past, one means of removing these objectionable odors was to blow the products with nitrogen dioxide; however, such treatment places an undesirable burden on the manufacturing facilities in respect to control of the exiting nitrogen oxides in order to avoid atmospheric pollution.

Accordingly, objects of this invention are to provide a method to produce a detergent-dispersant alkoxylated product of improved odor which is resistant to oxidative breakdowns in engine operation caused by the strains of high temperature and anti-pollution devices placed on lubricating oils containing said alkoxylated product.

Another object is to provide a detergent-dispersant alkoxylated product of improved odor and oxidation resistant properties and lubricating oil compositions thereof.

SUMMARY OF INVENTION

We have discovered and this constitutes our invention a method, sulfurized alkoxylated product resulting therefrom and lubricant compositions containing said sulfurized alkoxylated product wherein said method produces a novel sulfurized alkoxylated product of improved antioxidant and odor properties. Broadly, in the method comprising first contacting in the presence of a catalytic amount of sulfur, polyalkene with $P_2S_5$ to form polyalkene-$P_2S_5$ reaction product, secondly contacting the resultant polyalkene-$P_2S_5$ reaction product with steam to form an inorganic phosphorus acid containing steam hydrolyzed polyalkene-$P_2S_5$ reaction product, thirdly removing the inorganic phosphorus acids from the steam treated reaction product, fourthly contacting the inorganic acid free, steam hydrolyzed polyalkene-$P_2S_5$ reaction product with an alkylene oxide to form the alkoxylated derivative, the improvement which comprises the step selected from the group consisting of 1). Contacting the inorganic acid free, steam hydrolyzed polyalkene-$P_2S_5$ reaction product with added sulfur at an elevated temperature and subjecting the resultant product to said fourthly contacting and 2). Contacting the alkoxylated inorganic acid free, steam hydrolyzed polyalkene-$P_2S_5$ final reaction product with added sulfur at an elevated temperature, thereby forming the sulfurized, alkoxylated product of improved antioxidant and odor properties.

Hereinbefore and hereinafter the product formed by the method of the invention will also be referred to as the sulfurized alkoxylated product.

DETAILED DESCRIPTION OF THE INVENTION

More specifically, in a method comprising:
a. first contacting a polyalkene of an average molecular weight between about 500 and 50,000 with between about 5 and 40 wt. % (basis reaction mixture) of $P_2S_5$ in the presence of a catalytic amount of sulfur, e.g., between about 0.1 and 1 wt. % sulfur at a temperature between about 100° and 320°C., advantageously in an inert atmosphere, and diluting the final product with a mineral lubricating oil,
b. secondly contacting the resultant lube concentrate of the polyalkene-$P_2S_5$ reaction product with a stoichiometric excess of steam at a temperature between about 100° and 260°C., preferably in an inert atmosphere, to form a lube concentrate of inorganic phosphorus acid containing steam hydrolyzed polyalkene-$P_2S_5$ reaction product, c. thirdly removing inorganic phosphorus acid from the steam treated polyalkene-$P_2S_5$ reaction product to form the inorganic phosphorus acid free, steam hydrolyzed polyalkene-$p_2S_5$ reaction product, d. fourthly contacting the inorganic acid free, steam hydrolyzed polyalkene-$P_2S_5$ reaction product with an alkylene oxide of from 2 to 10 carbons at a temperature between about 180° and 220°C., preferably in an inert atmosphere utilizing a mole ratio of alkylene oxide to initial polyalkene of at least greater than about 1:1, preferably between about 1:1 and 1:5, the improvement which comprises the step selected from the group consisting of:

1. contacting the inorganic acid free, steam hydrolyzed polyalkene-$P_2S_5$ reaction product of step $c$ with added sulfur, preferably in an inert atmosphere, at a temperature of between about 180° and 300°C., preferably between 190° and 210°C., utilizing a mole ratio of initial polyalkene to added sulfur of between about 1:0.5 and 1:10, preferably between 1:1 and 1:3, and then contacting the resultant sulfur treated product in accordance with step $d$ to form the sulfurized alkoxylated detergent product of improved antioxidant and odor properties.

2. contacting the alkoxylated final product of $d$ with added sulfur, preferably in an inert atmosphere at a temperature between about 130° and 300°C., preferably between 150° and 200°C., utilizing a mole ratio of initial polyalkene to added sulfur of between about 1:0.5 and 1:10, preferably between 1:1 and 1:3, to form said sulfurized alkoxylated detergent of improved antioxidant and odor properties.

Step a

In Step a the alkenes from which the polyalkene hydrocarbon reactants are derived are normally of 2 to 10 carbons such as ethylene, propylene, butylene, isobutylene, pentylene, hexylene, heptylene, isooctylene and decylene. Examples of the polyalkene are polybutene (polyisobutylene, polybutylene), polypropene (polypropylene) and copolymers of alkenes such as propene-isobutene copolymer are preferred materials for reaction with $P_2S_5$. In general, the polyalkene polymer reactants in copolymers have an average molecular weight between about 500 and 50,000 but polymers and copolymers of a molecular weight between 600 and 2000 are preferred. An example of one preferred polyalkene is a polyisobutene polymer having an average molecular weight of between about 700 and 2000, most preferably about 1,200. The polyalkene reactant polymers contemplated herein are normally monoolefinic in nature.

The inert gas utilized to supply the non oxidizing atmosphere under the most preferred conditions in this and subsequent steps is usually nitrogen.

The consistency of the catalytic sulfur employed ranges from powder to coarse sand like particles with the finer consistencies being preferred.

At the end of this step, the polyalkene-$P_2S_5$ product is advantageously diluted with a mineral lubricating oil desirably of an SUS viscosity between about 50 and 1,000 to form a lube concentrate polyalkene-$P_2S_5$ reaction mixture. Normally, sufficient lube oil is utilized to form a concentrate having an oil content between about 10 and 90 wt. %, preferably between 25 and 75 wt. %. Examples of the mineral lubricating oil component contemplated herein are paraffin base, naphthene base or mixed paraffin base naphthene base distillates of residual oils. The lubricating mineral oil bases generally have been subjected to solvent refining to improve lubricity and viscosity temperature relationship as well as solvent dewaxing to remove waxy components and improve the pour of the oil. The preferred viscosities are normally between about 70 and 300 SUS at 100°F.

Step b

In Step b the steam is usually passed directly into the oil solution. Under advantageous conditions, at least about 1 mole of steam is employed per mole of polyalkene-$P_2S_5$ reaction product and the hydrolysis is normally conducted for a period of between about 1 and 20 hours.

Step c

The hydrolyzed product derived from Step b contains undesirable inorganic phosphorus acid by-products and they are removed by standard procedures. A number of different procedures are available for the removal of the inorganic sulfurous acid. In U.S. Pat. No. 2,951,835 and 2,987,512 removal of the inorganic phosphorus acid is effected by contact with synthetic anhydrous alkaline earth metal silicates and synthetic anhydrous alkali metal silicates respectively. Further U.S. Pat. No. 3,135,729 describes a process where inorganic phosphorus acids are removed from the hydrolyzed product by first drying the hydrolyzed product by passing an inert gas such as nitrogen therethrough at between about 120° and 200°C. and then contacting the inorganic acids with anhydrous methanol under mixing conditions at a temperature between about 40° and 80°C. in a methanol amount of between about 30 and 80 volume % based on the overall mixture, thereby forming an extract phase containing inorganic phosphorus acid and a mineral oil raffinate phase containing inorganic phosphorus acid free, steam hydrolyzed $P_2S_5$-polyalkene reaction product. During the methanol extraction procedure, superatmospheric pressure may be applied, e.g., up to about 50 psig in order to maintain the methanol in a liquid state. At the end of the methanol extraction step any methanol carried over into the raffinate phase is preferably removed, e.g., by stripping the raffinate with an inert gas at an elevated temperature.

Step d.

The inorganic phosphorus acid free, steam hydrolyzed polyalkene-$P_2S_5$ reaction product of Step C or the sulfurized version thereof is contacted with alkylene oxide under essentially atmospheric or superatmospheric pressures, e.g., between about 10 and 500 psig being advantageous with the lower alkene oxides. Prior to contact with the alkylene oxide, the reaction mixture is preferably blown with inert gas and continued at a low level to aid the introduction of the alkylene oxide. Excess alkylene oxide is desirably removed after completion of the reaction by blowing the reaction mixture at an elevated temperature generally with an inert gas such as nitrogen.

The alkylene oxides contemplated herein are represented by the formula:

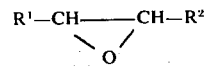

where $R^1$ and $R^2$ are hydrogen or aliphatic hydrocarbon radicals containing 1 to 6 carbons. Since there is no inorganic acid catalyst present such as inorganic phosphorus acid by-product (having been removed in Step c), the amount of alkylene oxide absorbed into the reaction system is essentially on a mole to mole basis in respect to initial polyalkene reactant. Alkylene oxide introduction is normally continued until absorption ceases usually in a period of 1 to 10 hours. Hereinbefore and hereinafter what is intended by the term "initial polyalkene" is the polyalkene initially employed in Step a.

Specific examples of the alkylene oxides contemplated herein are ethylene oxide, propylene oxide, 1,2-butylene oxide, 2,3-butylene oxide, 1,2-pentyleneoxide, 2,3-pentylene oxide, 1,2-hexylene oxide, 3-methyl-1,2-pentylene oxide, 2,3-octylene oxide, 4-methyl-2,3-octylene oxide, 4- methyl-1,2-hexylene oxide, and 3-methyl-1,2-butylene oxide.

If odor improvement is desired in addition to that afforded by the added sulfur improvement step, standard supplementary odor treatments may be employed for still better consumer acceptance of the product. One such method calls for the treatment of the unsulfurized product of Step d with nitrogen dioxide or a mixture of nitrogen dioxide and oxygen optionally diluted with inert gas such as nitrogen. The nitrogen dioxide and mixtures thereof are contacted, e.g., bubbled through with the Step d product at a temperature between about 65° and 150°C. until at least about 0.15 wt. % nitrogen dioxide is absorbed. Under advantageous conditions, nitrogen dioxide is diluted with air or inert gas such as nitrogen, carbon dioxide and the like in a volume ratio of about 1:99. The residual oxides of nitrogen are removed from the treated mixture by stripping with an inert gas such as nitrogen or air.

Improvement Sulfurization Step 1 or 2

In alternative improvement step 1 and 2 the added sulfur employed as in the case of catalytic sulfur utilized in Step a can be of a particle size ranging from powder to coarse sand with the finer consistencies being preferred.

In all the foregoing steps the ingredients are preferably kept in an agitated state, when feasible, e.g., via stirring in order to facilitate ingredient contact.

Sulfurized Alkoxylated Product And Lubricant Compositions Thereof

As heretofore stated, the sulfurized alkoxylated products produced in the aforedescribed procedure have usefulness as detergent-dispersants in automotive lubricating oils. They are normally present in lubricating oils in concentrations sufficient to impart detergent-dispersant properties thereto. In finished lubricants the concentration of the sulfurized alkoxylated product normally falls between about 0.1 and 10 wt. % with a concentration between about 1 and 5 wt. % preferred.

In lubricating oil formulations of the invention the lubricating base oils contemplated herein are those described in respect to aforedescribed Step b. Further, the base oil constitutes a major amount of the finished formulation, e.g., at least about 85 wt. % or more with the remainder of the formulation being the sulfurized alkoxylated product and supplementary additives to impart even greater oxidation resistance or other desirable properties thereto.

In respect to supplementary additives Viscosity Index (VI) improvers such as the polymethacrylates are normally included as are corrosion inhibitors and other products.

A widely used VI improver is polymethacrylate having the generaly formula:

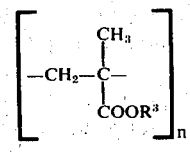

where $R^3$ is an aliphatic radical of from 1 to 20 carbons and n is an integer between about 600 and 35,000. One most suitable VI improver is the tetrapolymer of butyl methacrylate, dodecyl methacrylate, octadecyl methacrylate and dimethylamino ethyl methacrylate being present in a weight ratio in the polymer of between about 4/10/5/1. The VI improvers are normally employed in the finished lubricant product compositions in amounts between 0.1 and 3 wt. %.

One of the more commonly used supplementary lube oil corrosion inhibitor and supplementary antioxidant employed is divalent metal dialkyl dithiophosphate resulting from neutralization of a $P_2S_5$-alcohol reaction product with a divalent metal or divalent metal oxide. Barium and zinc dialkyl dithiophosphate are examples. Additional supplementary antioxidants that may be employed are polyalkylated diphenylamine and 2,2'-diethyl-4-t-octyldiphenylamine. These supplementary products are usually present in lubricating compositions in concentrations between about 0.1 and 3 wt. %.

A commonly used detergent-dispersant used as a supplement to the sulfonated alkoxylated products of the invention are the alkaline earth metal alkylphenolates such as barium nonylphenolate, barium dodecyl cresolate, calcium dodecylphenolate. Still other supplemental detergent-dispersants are the calcium carbonate overbased calcium alkylsulfonate formed by blowing a mixture of calcium hydroxide and calcium alkylsulfonate, (e.g., calcium alkylbenzene sulfonate of about 500 m.w.) with carbon dioxide to form a product having a total base number (TBN) of 50 or more, e.g., 300 to 400. These supplementary detergents are again usually present in the lubricating oil in concentrations between about 0.1 and 5 wt. %.

Still other ingredients found in the typical lubricant compositions contemplated herein are antifoamants such as the dimethyl silicone polymers in amounts of between about 10 and 1000 ppm.

As heretofore indicated, it has been unexpectedly discovered that employment of the sulfurization improvement step in the method contemplated herein, either immediately after the preparation of the inorganic phosphorus acid free, steam hydrolyzed polyalkene-$P_2S_5$ reaction product prior to alkoxylation or directly after the alkoxylation step, unexpectedly substantially improved the antioxidant properties of the sulfurized alkoxylated reaction product as well as the odor properties. This improvement in some instances may be sufficient to eliminate the need of the inclusion of antioxidant additives in the formulation in which the sulfurized product is present and further may in some instances eliminate the need for additional deodorization treatments. In any case, if an antioxidant and additional deodorization treatments are needed in respect to compositions containing the sulfurized alkoxylated products of the invention, the amount of antioxidant required is essentially less than if the non sulfurized product was employed and supplementary deodorization treatments can be substantially less harsh for equivalent results. The economic benefits from the elimination or reduction of supplementary antioxidant additive use and the elimination of added deodorization treatments or the reduction of the severity of such are obvious.

The following examples further illustrate the method, detergent product and lubricant compositions of the invention.

EXAMPLE I

This example illustrates one of the alternative methods of the invention and the sulfurized alkoxylated product resulting therefrom.

To a 5 liter 3 necked flask fitted with a thermometer, condenser, gas inlet tube and mechanical stirrer there was charged 1,320 grams (1.1 mole) of polyisobutene having an average molecular weight of about 1200, 222 grams (1.0 mole) of $P_2S_5$ and 11 grams (0.34 gram atoms) sulfur. The stirred mixture was heated to 230°C. and held at that temperature for 5 hours while maintained in a nitrogen atmosphere. The product was then cooled to 150°C. and 2,060 grams of naphthenic lubricating oil having an SUS viscosity of about 100 at 100°F. were charged. The mixture was then heated to 166°C. and hydrolyzed with steam for 10 hours. The resultant steam hydrolyzed product was then extracted with 2 liters of methanol at 60°C. and the raffinate was stripped to 150°C. with nitrogen blowing.

To a 3 liter 3-necked flask fitted with a stirrer, condenser, thermowell and thermocouple and gas inlet tubes there were charged 1,315 grams (0.5 mole) of stripped product and 32 grams (1 mole) of sulfur. The mixture was stirred and the temperature was gradually raised to 200°C. under a continuous nitrogen purge and maintained at this temperature for 6 hours. The sulfur treated mixture was allowed to cool to 90°C. and ethylene oxide bubbled therethrough until a vigorous reflux was noted in the exit dry ice condenser. The amount of ethylene oxide absorbed was 44 grams (1.0 mole). The flask was purged with nitrogen at 93°C. for 1 hour and the purged material was then treated with nitrogen dioxide by bubbling nitrogen dioxide therethrough for a period of 2 hours followed again by a nitrogen purge. The product was then filtered through diatomaceous earth. Analysis of the product found it to be a ~ 40 wt. % lube oil concentrate of sulfurized, monoethoxylated, inorganic phosphorus acid free, steam hydrolyzed polyisobutene (1,200 m.w.)-$P_2S_5$ reaction product having a sulfur content of 2.08 wt. %, a phosphorus content of 0.83 wt. %, a Neut. No. of 1.6, a Hydroxyl No. of 20.

EXAMPLE II

The procedure of Example I was repeated with the exception that sulfurization took place at 175°C. for a 4 hour period. The resultant product was identified as ~ 40 wt. % lube oil concentrate of sulfurized, monoethoxylated, inorganic phosphorus acid free, steam hydrolyzed polyisobutene (1200 m.w.)-$P_2S_5$ reaction product having a sulfur content of 1.79 wt. %, a phosphorus content of 1.03 wt. %, a Neut. No. of 3.3 and a Hydroxyl No. of 24.

EXAMPLE III

This example illustrates the sulfurized alkoxylated product method and the alternative method of the invention wherein the sulfurization is conducted after alkoxylation.

To a 5 liter 3 necked flask fitted with a stirrer, condenser, thermowell, thermocouple and gas inlet tube there were charged 1320 grams (1.1 mole) of polyisobutene of a molecular weight of about 1200, 222 grams (1.0 mole) $P_2S_5$ and 11 grams (0.34 gram atoms) sulfur. The resultant mixture was heated to 230°C. and held at that temperature for 5 hours while passing nitrogen therethrough to maintain the reaction mixture under a blanket of nitrogen. The product was then cooled to 150°C. and 2,060 grams of naphthenic lubricating oil having an SUS viscosity of about 100 at 100°F. were introduced. The mixture was then heated to 166°C. and hydrolyzed with steam therein for a period of 10 hours. Steaming was conducted in a nitrogen atmosphere and the resultant product was dried by the passage of nitrogen therethrough at 150°C. The hydrolyzed product was extracted with ~ 40% volume of methyl alcohol at 60°C. to give a methanol extract containing inorganic phosphorus acid and a raffinate containing inorganic phosphorus acid free, steam hydrolyzed polybutene (1,200 m.w.)-$P_2S_5$ reaction product. The resultant raffinate product was heated to a temperature of 150°C. for a ~ 2 hour period. The mixture was then cooled to 93°C. and ethylene oxide was bubbled therethrough until a vigorous reflux was noted in the dry ice exit condenser indicating that ethylene oxide was no longer being absorbed. The flask was then purged with nitrogen for a 1 hour period followed by a nitrogen dioxide blowing at 93°C. until about 0.2 wt. % nitrogen dioxide was absorbed. The resultant product was filtered through diatomaceous earth and identified as the lube concentrate of monoethoxylated polyisobutene (1,200 m.w.)-$P_2S_5$ reaction product.

To a 3 necked flask as described above there was charged 700 grams (0.25 mole) of the filtered ethoxylated product together with 16.0 grams (0.5 gram atom) sulfur. The mixture was stirred and the temperature raised gradually to 175°C. under a continuous nitrogen purge and maintained at this temperature for a 4 hour period. The resultant product was analyzed and determined to be a ~ 40 wt. % naphthenic lubricating oil concentrate of sulfurized ethoxylated, inorganic phosphorus acid free, steam hydrolyzed polyisobutene (1200 m.w.)-$P_2S_5$ reaction product having a sulfur content of 1.87 wt. %, phosphorus of 1.09 wt. %, Neut. No. of 1.52 and Hydroxyl No. of 14.

EXAMPLE IV

This example illustrates a comparative procedure, comparative product and comparative lubricant composition of the prior art.

The procedure of Example III was repeated with the exception that the final sulfurization step was omitted. Analysis of the product determined it to be ~ 40 wt. % naphthenic lubricating oil concentrate of a monoethoxylated inorganic phosphorus acid free, steam hydrolyzed polyisobutene (1,200 m.w.)-$P_2S_5$ reaction product having a sulfur content of 0.86 wt. %, a phosphorus content of 1.06 wt. %, a Neut. No. of 3.1 wt. % and a Hydroxyl No. of 14.

EXAMPLE V

This example illustrates examples of the contemplated finished automotive lubricating oil compositions containing the sulfurized alkoxylated product and further illustrates the superiority of the sulfurized alkoxylated product as opposed to its unsulfurized counterpart in respect to antioxidant properties and odor while being essentially equivalent to the unsulfurized counterpart in respect to detergent-dispersant properties.

To test the lubricant compositions of the invention four tests were employed briefly described as follows:

BENCH OXIDATION TEST

The test oil sample in an amount of 160 mls. is placed on a stainless steel beaker maintained in a oil bath at 177°C. and the sample is heated at that temperature for a three-day period 12 hours each day. The kinematic viscosity of the sample is measured at 38°C. after heating at the 24th 48th and 72nd hour periods. The degree of oxidative break-down of the test sample during heating is relatively proportional to the increase in the viscosity of the test sample during heating.

ENGINE OXIDATION TEST

This test is used to evaluate motor oils with respect to their ability to prevent high temperature oxidative thickening. A single cylinder spark ignition engine of 42.5 CID equipped with a fuel injection system, an air flow meter and a positive crankcase ventilation system is employed. Regular leaded fuel is used to operate the engine under the following conditions:

| | |
|---|---|
| Test Duration, Hrs. | 50 |
| Speed, RPM | 3200 ± 25 |
| Fuel Flow, lbs./hr. | 6.0 ± 0.1 |
| Air:Fuel Ratio | 16:1 |
| Jacket - In, °F. | 240 ± 2 |
| Jacket - Out, °F. | 250 ± 2 |
| Oil Gallery, °F. | 320 ± 2 |
| Intake Air After Heater, °F. | 115 |
| Exhaust Back Pressure, in. Hg. | 1.0 ± .1 |
| Crankcase Vac., in. $H_2O$ | 2.0 ± .2 |
| Engine Ventilation, CFH | 20 ± 2 |
| Oil Pressure, PSI | 40 ± 2 |
| Oil Charge, lbs. | 3.0 ± .05 |
| Spark Advance, °BTC | 35 |

Motor oil performance is based on used oil degradation as determined by Differential Infrared analysis at 5 hour intervals. Performance is expressed in terms of hours to break, that is, the test time elapsed until the oil shows a sharp increase in the slope of the Differential Infrared at 5.8 $\mu$ vs. time curve. The greater the number of hours to "break" the greater the resistance of the composition tested to oxidative thickening.

ODOR TEST

A panel of individuals rate the odor of the test sample as to the degree of sulfur odor present. A rating of 10 denotes no sulfur odor and a rating of 1 denotes harsh hydrogen sulfide odor present. The intermediate ratings are the degree of pungency of the sulfur odor lessening as the scale increases. The ratings given by each of the test panel members are averaged and the average value reported as the odor rating.

BENCH SLUDGE TEST (BST)

This test measures the relative detergency properties of the test sample. The test procedure comprises introducing into 20 cc. bottles portions of the sample composition titanium oxide (6 wt. %) in oil, aqueous and hydrocarbon engine blowby. The bottles are then agitated at elevated temperature for a period of time and a portion thereof is then centrifuged and observations are made of the precipitated solid sediment bottom phase, the intermediate phase comprising oil plus dispersed sediment and a clear top oil phase. The smaller the bottom sediment and top clear oil phase and the larger the dispersed intermediate phase, the greater the effectiveness of the dispersancy of the lubricant composition in maintaining the engine blowby products in the intermediate suspension. Test results (listed in Table III) refer to the depth of the bottom sediment in millimeters. The smaller the number (in. mm.) the more effective the dispersant. A non dispersant oil would give a rating in excess of 3 mm.

EXAMPLE Va

The lube concentrates of the ethoxylated products prepared in Examples I, II, III and IV were compounded into finished SAE 10W-30 type formulations of the following analysis:

TABLE I

| | Wt. % | | | |
|---|---|---|---|---|
| Ingredients | A Ex. I | B Ex. II | C Ex. III | D Ex. IV |
| Refined paraffinic distillate oil (~330 SUS at 100°F.) | 89.1 | 89.1 | 89.1 | 89.1 |
| Zinc isopropylmethylisobutyl carbinol dithiophosphate | 0.90 | 0.90 | 0.90 | 0.90 |
| $CO_2$ overbased calcium alkylated benzene sulfonate (TBN 300) | 2 | 2 | 2 | 2 |
| Mineral oil concentrate containing 40 wt. % copolymer of lauryl and stearyl methacrylates (8:2 wt. ratio) | 0.5 | 0.5 | 0.5 | 0.5 |
| Example I Conc. | 7.5 | — | — | — |
| Example II Conc. | — | 7.5 | — | — |
| Example III Conc. | — | — | 7.5 | — |
| Example IV Conc. | — | — | — | 7.5 |

Further analysis of the finished compositions of A, B, C and D found them to contain 0.1 Wt. % zinc and 0.35 wt. % calcium.

Foregoing formulations A, C and D were tested in the Bench Oxidation Test and as can be seen from the data in following Table II representative formulations A and C were substantially superior to comparative formulation D.

TABLE II

| | Viscosity (Min. 38°C.) | | |
|---|---|---|---|
| Formulation | 24th Hr. | 48th Hr. | 72nd Hr. |
| A | 37.9 | 86.0 | 153.8 |
| C | 40 | 90 | 160 |
| D | 76.8 | 138.4 | 214.8 |

Formulations A, B, C and D were tested in the Bench Sludge Test and as can be seen from the data in following Table III representative formulations A, B and C are essentially equivalent to comparative formulation D in respect to dispersancy properties:

TABLE III

| Formulation | Sediment Depth (mm.) |
|---|---|
| A | 0.5 |
| B | 0.4 |
| C | 0.7 |
| D | 0.7 |

Formulations A, B, C and D were also subjected to the odor test and as can be seen from following Table IV representative formulations A, B and C were judged superior in odor to comparative formulation D:

TABLE IV

| Formulation | Odor Rating |
|---|---|
| A | 4 |
| B | 3 |
| C | 4 |

TABLE IV-continued

| Formulation | Odor Rating |
|---|---|
| D | 6 |

EXAMPLE Vb

The following finished SAE formulations utilizing the sulfurized alkoxylated lube oil concentrate of Examples I and III and the unsulfurized comparative product of Example IV were prepared and their compositions are set forth below in following Table V with "DOD" representing a known antioxidant additive comprising 33-1/3 wt. % 2,2'-diethyl-4-tertiary octyl diphenylamine and 66-2/3 wt. % 2,2'-diethyl-4,4-dioctyl diphenylamine:

TABLE V

| | Weight % | | |
|---|---|---|---|
| Ingredients | E Ex. I | F Ex. III | G Ex. IV |
| Refined paraffinic distillate oil (125 SUS at 100°F.) | 91.6 | 91.6 | 91.6 |
| Zinc isopropylmethyl isobutyl carbinol dithiophosphate | 0.90 | 0.90 | 0.90 |
| DOD | — | — | 0.35 |
| Example I Conc. | 7.5 | — | — |
| Example III Conc. | — | 7.5 | — |
| Example IV Conc. | — | — | 7.5 |

The prepared fnished formulations were subjected to the Engine Oxidation Test and as can be seen by the data in following Table VI representative E and F were superior to the comparative oxidation inhibited composition G in resistance to oxidation:

TABLE VI

| Formulation | Hrs. to Break Visc. Curve | Hrs. to Break 5.8 Curve |
|---|---|---|
| E | 33 | 25 |
| F | 32 | 26 |
| G | 29 | 22 |

We claim:

1. A method of preparing a lubricating oil concentrate of a detergent-dispersant sulfurized alkoxylated product consisting essentially of:
   a. first contacting a polyalkene of an average molecular weight between about 500 and 50,000 with $P_2S_5$ in the presence of between about 0.1 and 1 wt. % sulfur at a temperature between about 100 and 320°C., said $P_2S_5$ comprising between about 5 and 40 wt. % of the reaction mixture,
   b. secondly diluting the polyalkene-$P_2S_5$ with mineral lubricating oil to form a lube concentrate of between about 10 and 90 wt. % of said lubricating oil,
   c. thirdly contacting the polyalkene-$P_2S_5$ lube concentrate with steam at a temperature between about 100 and 260°C. utilizing at least about a mole ratio excess of steam in respect to said polyalkene-$P_2S_5$ reaction product,
   d. fourthyl removing inorganic phosphorus acid from the steam treated polyalkene-$P_2S_5$ concentrate,
   e. fifthly contacting the inorganic acid free, steam hydrolyzed polyalkene-$P_2S_5$ concentrate with an alkylene oxide of the formula:

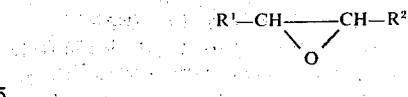

where $R^1$ and $R^2$ are hydrogen or an alkyl containing 1 to 6 carbon atoms in a mole ratio of said inorganic phosphorus acid free, steam hydrolyzed $P_2S_5$-polyalkene reaction product to said alkylene oxide of at least about 1:1, the improvement which comprises the step of contacting the alkoxylated inorganic free, steam hydrolyzed polyalkene-$P_2S_5$ reaction product of Step e with added sulfur at a temperature between about 130° and 300°C. utilizing an initial polyalkene:added sulfur mole ratio of between about 1:0.5 and 1:10 to form said sulfurized alkoxylated product.

2. A method in accordance with claim 1 conducted in an inert atmosphere.

3. A method in accordance with claim 2 wherein said polyalkene is a polybutene of a molecular weight between about 500 and 2,000 and said alkylene oxide is ethylene oxide.

4. A method in accordance with claim 2 wherein said polyalkene is polyisobutene of a molecular weight of about 1200 and said alkylene oxide is ethylene oxide.

5. A finished lubricating oil composition comprising a major amount of lubricating oil and between about 0.1 and 10 wt. % of a detergent dispersant sulfurized alkoxylated product in a lubricating oil concentrate thereof, said concentrate prepared by the method consisting essentially of:
   a. first contacting a polyalkene of an average molecular weight between about 500 and 50,000 with $P_2S_5$ in the presence of between about 0.1 and 1 wt. % sulfur at a temperature between about 100° and 320°C., said $P_2S_5$ comprising between about 5 and 40 wt. % of the reaction mixture,
   b. secondly diluting the polyalkene-$P_2S_5$ with mineral lubricating oil to form a lube concentrate of between about 10 and 90 wt. % of said lubricating oil,
   c. thirdly contacting the polyalkene-$P_2S_5$ lube concentrate with steam at a temperature between about 100° and 260°C. utilizing at least about a mole ratio excess of steam in respect to said polyalkene-$P_2S_5$ reaction product,
   d. fourthly removing inorganic phosphorus acid from the steam treated polyalkene-$P_2S_5$ concentrate,
   e. fifthly contacting the inorganic acid free, steam hydrolyzed polyalkene-$P_2S_5$ concentrate with an alkylene oxide of the formula:

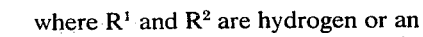

where $R^1$ and $R^2$ are hydrogen or an alkyl containing 1 to 6 carbon atoms in a mole ratio of said inorganic phosphorus acid free, steam hydrolyzed $P_2S_5$-polyalkene reaction product to said alkylene oxide of at least about 1:1, the improvement which comprises the step of contacting the alkoxylated inorganic acid free, steam hydrolyzed polyalkene $P_2S_5$ reaction product of step e with added sulfur at a temperature between about 130° and 300 °C. utilizing an initial polyalkene: added sulfur mole ratio of between about 1:0.5 and 1:10 to form said sulfurized alkoxylated product.

6. A composition in accordance with claim 5 wherein said method is conducted in an inert atmosphere.

7. A composition in accordance with claim 5 wherein in said method polyalkene is polybutene of a molecular weight between about 500 and 2,000 and said alkylene oxide is ethylene oxide.

8. A composition in accordance with claim 5 wherein in said method said polyalkene is polyisobutene of a molecular weight of about 1200 and said alkylene oxide is ethylene oxide.

* * * * *